United States Patent [19]

Nicolas et al.

[11] Patent Number: 5,895,752
[45] Date of Patent: Apr. 20, 1999

[54] METHOD FOR RAPID DIAGNOSIS OF AEROBIC BACTERIA PRESENT IN A BIOLOGICAL MEDIUM

[75] Inventors: Marie-Helene Nicolas, Paris; Fabrice Bru, Suresnes, both of France

[73] Assignee: Assistance Publique, Paris, France

[21] Appl. No.: 08/175,047

[22] Filed: Dec. 29, 1993

[30] Foreign Application Priority Data

Dec. 29, 1992 [FR] France .................................. 9215854

[51] Int. Cl.[6] .................................................. C12Q 1/24
[52] U.S. Cl. .................................. 435/30; 435/29; 435/34; 435/40.5; 435/40.51
[58] Field of Search ........................... 435/29, 30, 34, 435/40.5, 40.51; 73/53.01, 61.63, 61.65

[56] References Cited

U.S. PATENT DOCUMENTS

| 4,632,902 | 12/1986 | Waters et al. | 435/29 |
| 4,693,972 | 9/1987 | Mansour et al. | 435/34 |
| 4,992,365 | 2/1991 | Hyman | 435/34 |

OTHER PUBLICATIONS

G.L. Dorn, "Blood Culture Technique Based on Centrifugation: Clinical Evaluation", Journal of Clinical Microbiology, vol. 3, Mar. 1976, pp. 258–263.

C.J. Shanholzer et al., "Concentrated Gram Stain Smears Prepared with a Cytospin Centrifuge", Journal of Clinical Microbiology, vol. 16, No. 6, Dec. 1982, pp. 1052–1056.

Davis, et al. Microbiology. 3rd. Ed. (1980) pp. 64–67.

*Primary Examiner*—Lien Tran
*Attorney, Agent, or Firm*—Jacobson, Price, Holman & Stern, PLLC

[57] ABSTRACT

A method for the rapid diagnosis of aerobic bacteria present in a biological medium comprising successively:

a) a rapid culture under aerobic conditions of a sample of the biological medium, with stirring, b) a rapid centrifugation in order to recover the bacteria from the centrifugation pellet, c) the projection, by centrifugation, of the pellet thus obtained onto a support d) the revealing of bacteria on the support.

3 Claims, No Drawings

METHOD FOR RAPID DIAGNOSIS OF AEROBIC BACTERIA PRESENT IN A BIOLOGICAL MEDIUM

The present invention relates to a method for the rapid diagnosis of aerobic bacteria present in a biological medium and especially in blood.

In spite of antibiotics, septicemias remain a major cause of mortality. During the past few years, it has been proposed to treat septicemias and septic shocks caused by Gram negative bacteria using anti-endotoxin monoclonal antibodies. However, these treatments are expensive and it is therefore logical to prescribe them only to patients who are affected by a septicemia caused by Gram-negative bacteria. Demonstrating the existence of Gram-negative bacteria in blood can be done by only two routes: assessing the endotoxin or detecting the Gram-negative bacteria.

It so happens however that the diagnostic methods used for this latter route give responses which are much too late given the existing need to rapidly administer anti-endotoxin antibodies for them to be effective. Thus, conventional methods using cultures do not permit a diagnostic in less than 12 hours.

Diagnostic methods using operations for lysis and centrifugation of blood samples before inoculation of the said sample have been especially described (see for example G. Dorn et al., J. Clinical Microbiology, 1976, 3: 258–263 and N. Henry et al., J. Clinical Microbiology, 1983, 17: 864–869). However, the diagnosis always involves not[sic] a culture with a minimum incubation time of 18 hours.

Methods comprising a detection of bacterial growth by radiometry have also been described. The detection can however only be performed within a minimum of 12 hours.

The present invention aims to provide a method for the rapid, that is to say within a maximum of 5 hours, diagnosis of the aerobic bacteria present in a biological medium, especially in blood, even at very low concentrations (0.1 to 10 CFU/ml).

The subject of the present invention is thus a method for the rapid diagnosis of aerobic bacteria present in a biological medium comprising successively:

a) a rapid culture (maximum 4 hours) under aerobic conditions of a sample of the biological medium, with stirring, b) a rapid centrifugation in order to recover the bacteria from the centrifugation pellet, c) the projections by centrifugation, of the pellet thus obtained onto a support d) the revealing of bacteria on the said support.

The subject of the present invention is more particularly a method for the diagnosis of aerobic bacteria present in blood comprising successively:

a) a culture under aerobic conditions of a blood sample, with stirring, b) a separation of red blood cells by slow centrifugation and a recovery of the supernatant, c) a lysis of the white blood cells in the supernatant, d) a rapid centrifugation of the medium thus obtained in order to recover the bacteria in the centrifugation pellet, e) the projection, by centrifugation, of the pellet thus obtained onto a support, f) the revealing of the bacteria on the said support.

The first stage of the method according to the invention is a culture of a sample, for example of 8–10 ml of blood, with vigorous stirring, preferably with very vigorous stirring in the presence of oxygen, for example in the presence of air. This stirring may be performed at speeds of the order of 100 to 400 revolutions per minute, for example 250 revolutions per minute. This stage is contrary to all that was recommended up until now. Indeed, in general, the stirring is inexistent or low and of very short duration in order to allow deposition of the red blood cells. In the present invention, the stirred culture is generally performed for a period of 2 to 4 hours, it being possible for this period to be shorter the higher the bacteria concentration.

In the absence of such a stirring, the limit for bacteria which can be detected is much higher and the time for results to be obtained is double. Thus, in the absence of stirring and using the same successive stages, only concentrations of a minimum of $10^2$ CFU of *Escherichia coli*/ml of blood can be detected and only after 8 hours of culture, whereas by carrying out the culture with stirring for 4 hours, *Escherichia coli* concentrations as low as 0.1 CFU/ml can be detected.

The stage for separation of the red blood cells by slow centrifugation can be performed especially at 200–300 g for a period of the order of 15 minutes.

The stage for lysis of the white blood cells can be performed as described by N. Henry (cited above) using the product contained in the Isolator tubes or any other product permitting lysis, such as saponin (final concentration of 0.2%). To this end, the product permitting the lysis is added directly to the supernatant and the whole is intimately mixed, for example by means of a vortex for 1 minute.

The stage for rapid centrifugation of the medium having undergone the lysis is performed in order to concentrate the bacteria This centrifugation may be performed at 4000–5000 g for 10 minutes.

The stage for projection, by centrifugation of the pellet previously obtained, onto a support can be performed especially using an apparatus called Cytospin (see in particular C. Shanholtzer et al., J. Clinical Microbiology, 16, 6, 1052, 1982) or any other centrifugation principle. This apparatus makes it possible to project and to concentrate the bacteria contained in the pellet over a small surface area of a glass slide, that is to say over a circle about 4 mm in diameter, thus making it possible to reveal the bacteria on the support. This revealing can be performed in general by Gram staining.

The method according to the invention was developed using 3 strains of aerobic bacteria encountered in nosocomial infections *Escherichia coli*, *Pseudomonas aeruginosa* and *Acinetobacter baumanii*.

These bacteria were cultured on agar for 18 hours under aerobic conditions. Colonies were collected and diluted in 2 ml of sterile distilled water and bacteria concentrations of $5 \times 10^6$ to $5 \times 10^8$ CFU/ml were obtained. 10 ml blood samples were inoculated with 0.1 ml of the $10^{-5}$ and $10^{-6}$ dilutions for each species, the density of bacteria in the samples being 0.05 to 5 CFU/ml.

The blood samples (10 ml) were transferred into hemoculture flasks containing 20 ml of culture broth (Hemoline performance Biomérieux S.A.) with 0.025% of sodium polyanetholsulfonate and incubated with stirring (250 revolutions per minute (Rotatest, Bioblock) for 4 hours at 37° C.

Each culture was then subjected to a centrifugation at 250 g for 15 minutes at 20° C. The supernatant was collected and in order to perform the lysis of the white blood cells, the Isolator (Dupont) compound or saponin at the final concentration of 0.2% was added. The mixture was stirred on a Vortex for 1 minute and then centrifuged at 4500 g for 10 minutes. After removal of the supernatant, the entire pellet was subjected to a centrifugation at 192 g for 10 minutes in a cytocentrifuge (Cytospin 2, Shandon) in order to obtain on a glass slide a smear 4 mm in diameter. The Gram staining was performed on this sample and examined under an immersion microscope.

It was thus possible to detect the presence of *E. coli* at the concentration of 0.1 CFU/ml in a blood sample, of *P. aeruginosa* at the concentration of 0.3 CFU/ml and of *A. baumanii* at the concentration of 1.5 CFU/ml.

In addition, in the absence of antibiotics in the blood samples, the method results in detection of the morphology of the bacteria thus permitting a diagnostic orientation with respect to the type of species. Thus, *E. coli* is recognizable in the form of a thick rod, *P. aeruginosa* in the form of a thin and elongated rod, *A. baumanii* in the form of *coccobacilli*. This is an additional advantage of the method since it permits the clinician to choose the antibiotic treatment more precisely.

Finally, on the pellet of red blood cells separated by means of slow centrifugation it is possible to perform an antibiogram the same days hence a substantial time gain.

It should be noted that the method applies mot only to the diagnosis of *Pseudomonas aeruginosa*, Acinetobacter and *Escherichia coli* but also to other enterobacteria such as *Klebsiella pneumonias*, other Gram-negative bacilli including *Haemophilus influenzae* which is a germ requiring growth factors, Gram-negative cocci such as *Neisseiria meningitidis* and finally Gram-positive cocci such as *Staphylococcus aureus*, Enterococcus, β-hemolytic *streptococci*.

The application of the method to blood collected from 39 patients considered clinically septicemic or in septic shock made it possible to calculate the sensitivity and the specificity of the method with reference to conventional hemocultures [Flacon hemoline anaérobie (anaerobic hemoline flask) from BioMérieux, Marcy l'Etoile] and to Isolator (Merck) For these two methods, direct culturing or subculturing were performed on chocolate agar incubated under a $CO_2$ atmosphere (5%) and on blood agar incubated under aerobic conditions.

Table I gives a list of bacterial species which were isolated, the initial blood concentration evaluated by the Isolator culture and the morphological and Gram staining results given by the rapid diagnostic method according to the invention.

TABLE 1

| Case | Species | Blood Concentration CFU/ml | Morphology and Gram evaluated after rapid diagnosis |
|------|---------|---------------------------|------------------------------------------------------|
| 7 | P. aeruginosa | 0.1 | Gram-negative bacillus |
| 8 | S. aureus | 0.5 | Cluster of Gram-positive cocci |
| 9 | P. aeruginosa | 0.8 | Gram-negative Bacillus |
| 22 | enterococcus | 2.8 | Gram-positive cocci in chains |
| 32 | E. coli | 32 | Gram-negative bacilli |
| 33 | E. coli | 2.5 | Gram-negative bacilli |
| 35 | Serratia Spp | 7.1 | Gram-negative bacilli |
| 38 | Bacteroides fragilis | — | Gram-negative bacillus |

It should be noted that for case 38, the conventional hemocultures under anaerobic conditions but not the Isolator made it possible to isolate a strain of *Bacteroides fragilis* (anaerobic bacterium). Using the rapid diagnostic method, Gram-negative bacilli were found to be present. Using the latter method, the culture which is performed under aerobic conditions was normally not able to permit the multiplication of the strain. This would imply that the initial concentration of *Bacteroides fragilis* in the patient's blood was high and sufficient for the simple bacteria concentration stage to have made it possible to detect them by Gram staining.

Furthermore, for 5 cases whose blood cultures remained negative by the conventional methods, the rapid diagnostic method was positive. In 4 cases, Gram-negative bacilli were found to be present and for the last, clusters of rare Gram-positive cocci were found to be present. For one of the cases with Gram-negative bacilli, it should be noted that the bacilli were highly polymorphic and in very large quantity whereas in the other cases, the quantity of bacilli was low as in the case of Gram-positive cocci.

The rapid method also made it possible to detect the presence in the patient's blood of bacilli which were abnormal in morphological terms (non-long-shaped deformed bacilli) and in terms of Gram staining (granulation, inhomogeneous staining, Gram-positive and Gram-negative). These "abnormal" bacilli are, on the one hand, not capable of being cultured and, on the other hand, also present in the blood of healthy subjects. Unlike healthy subjects, the quantity of these "abnormal" bacilli is sometimes higher in subjects presumed clinically septicemic and/or in septic shock.

These latter results as a whole show that the rapid diagnostic method, by virtue of its bacteria concentration stage by centrifugation is not only capable of detecting viable bacteria but also non-viable bacteria.

It was possible for the method according to the invention with stirred and rapid culture to be extended to other types of samples other than blood. Indeed, this method is also efficient for detecting the presence of bacteria in spinal fluid (SF). The first experiments performed in vitro show that a culture of 1 ml of SF in 10 ml of culture broth (hemoline) is detected as positive by the rapid method when the SF was contaminated in vitro with 10 CFU/ml of *S. aureus, S. epidermidis, E. coli, K. pneumoniae, P. aeruginosa, Listeria monocytogenes* or *streptococcus*.

However, in order to apply this method to SF, a few modifications were made:
- there is no longer any slow centrifugation since there are not many red blood cells in the SF,
- the lysis was not performed since the lysis of leucocytes in a large quantity in the SF increases the background during the Gram staining.

We claim:

1. A method for revealing bacteria in a clinical sample from a patient comprising the steps of, in succession:

culturing the clinical sample in broth medium for a period of up to 4 hours under aerobic conditions, with stirring;

centrifugating the sample at 4000–5000 g to concentrate bacteria present in the sample in a pellet;

projecting the pellet onto a bacteria detection support by centrifugation; and treating the pellet to reveal bacteria present; the method requiring a maximum of 5 hours.

2. A method for revealing bacteria in a fluid clinical sample from a patient comprising the steps of, in succession:

culturing the fluid clinical sample in broth medium for a period of up to 4 hours under aerobic conditions, with stirring;

lysing white blood cells in the sample;

centrifugating the sample at 4000–5000 g to concentrate bacteria present in the sample in a pellet;

projecting the pellet onto a bacteria detection support by centrifugation; and treating the pellet to reveal bacteria present; the method requiring a maximum of 5 hours.

3. A method for revealing bacteria in a blood sample from a patient comprising the steps of, in succession:

culturing the blood sample in broth medium for a period of up to 4 hours under aerobic conditions, with stirring;

separating red blood cells from the blood sample by centrifugating the blood sample at 200–300 g and recovering resulting supernatant;

lysing white blood cells in the supernatant;

centrifugating the supernatant at 4000–5000 g to concentrate bacteria present in the supernatant in a pellet;

projecting the pellet onto a bacteria detection support by centrifugation; and treating the pellet to reveal bacteria present; the method requiring a maximum of 5 hours.

* * * * *